United States Patent [19]

Escher et al.

[11] 4,248,742
[45] Feb. 3, 1981

[54] USE OF A HYDROXYLIC BICYCLIC DERIVATIVE AS PERFUMING INGREDIENT

[75] Inventors: Sina D. Escher, Le Lignon; Anthony F. Morris, Gingins, both of Switzerland

[73] Assignee: Firmenich SA, Geneva, Switzerland

[21] Appl. No.: 75,416

[22] Filed: Sep. 14, 1979

[51] Int. Cl.³ ............................................. C11B 9/00
[52] U.S. Cl. .......................... 252/522 R; 252/174.11; 428/358
[58] Field of Search ................................... 252/522 R

[56] References Cited

U.S. PATENT DOCUMENTS

| | | | |
|---|---|---|---|
| 3,870,659 | 3/1975 | Bozzato et al. | 252/522 R |
| 3,928,246 | 12/1975 | Stadler et al. | 252/522 R |

OTHER PUBLICATIONS

Steffen Arctander, Perfume and Flavor Materials of Natural Origin, Published by the Author, Denmark, p. 62.6, 1960.

Chem. Ab. 67:106106n, 1967.
Steffen Arctander, Perfume and Flavor Chemicals, Published by Author, Montclair, N.J. Monograph 824, 1969.

*Primary Examiner*—Veronica O'Keefe
*Attorney, Agent, or Firm*—Pennie & Edmonds

[57] ABSTRACT

Process for imparting, enhancing or modifying the ambery odorous note in perfumes, perfume compositions or artificial essential oils, which comprises adding thereto a compound of formula

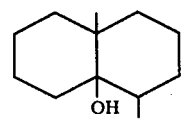

(I)

at a concentration of from about 1 to 100 parts per million by weight based on the total weight of the thus obtained material.

6 Claims, No Drawings

USE OF A HYDROXYLIC BICYCLIC DERIVATIVE AS PERFUMING INGREDIENT

THE INVENTION

The present invention relates to the field of perfumery, in particular it relates to a process for imparting, enhancing or modifying the ambery odorous note in perfumes, perfume compositions or artificial essential oils, which comprises adding thereto a compound of formula

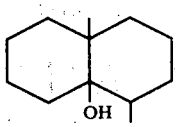

(I)

at a concentration of from about 1 to 100 parts per million by weight based on the total weight of the thus obtained material.

The invention provides a perfume composition or an artificial essential oil containing as active perfuming ingredient a compound of formula (I).

The invention provides also an artificial essential oil of Angelica roots which comprises having added thereto a compound of formula (I).

BACKGROUND OF THE INVENTION

Formula (I) is deemed to define isomers of 2,6-dimethylbicyclo[4.4.0]decan-1-ol, namely the isomers of formula

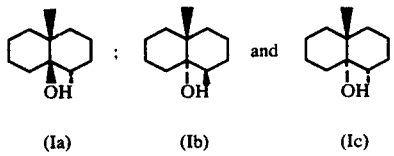

(Ia)     (Ib)     (Ic)

(−)-Geosmin (Ic), which is a known compound, was isolated for the first time by Gerber et al. [Appl. Microbiol. 13, 935 (1965)] as a metabolite of several microorganisms of the family of actinomycetes. It occurs also in nature as a metabolite of certain algae [see T. Kikuchi et al., Chem. pharm. Bull., 21, 2342 (1973)] and it has been considered as the compound responsible for the desagreable odour of public water supplies. Its odour has been defined by most of the authors as being earthy-musty and, so far, no utilization of it has been nor mentioned nor suggested. We have now unexpectedly discovered that (−)-geosmin, as well as its isomers of formula (Ia) and (Ib) possessed very useful odorous properties and, consequently, these compounds could be advantageously used in numerous perfume compositions of various nature.

PREFERRED EMBODIMENTS OF THE INVENTION

The said compounds develop amber-like or woody notes of a particular intensity and distinction. Their use could be envisaged not only as ingredients in perfume compositions of luxury type but also for the perfuming of products such as cosmetics, soaps in particular, detergents or house-hold materials in general. Owing to their specific odorous properties, compounds (I) are perfectly adapted to the creation of perfumes containing perfume coingredients of oriental, amber, aromatic or herbal type.

Compounds (I) can also be utilized for the reconstruction of natural essential oils. We have found in fact that they can be advantageously used for the reconstitution of Angelica roots oil, one of the major natural ingredients in perfumery.

The proportions at which the said compounds can be utilized in accordance with the invention vary within a wide range. Typically, there are used concentrations of from about 1 to about 100 ppm (parts per million) by weight based on the total weight of the resulting perfumed material. Of course, it has to be understood that the above given values are not deemed to be interpreted restrictively and concentrations lower or higher than those indicated can be used depending on the nature of the materials to be perfumed and that of the coingredients in a given perfume composition.

The compounds of formula (I) can be prepared in accordance with known processes, e.g. in accordance with the process described by Marshall et al. [see: J. Org. Chem., 33, 2593 (1968)] and Ayer et al. [see: Canad. J. Chem., 54, 3276 (1976)].

By applying the method of Marshall, we could obtain an isomeric mixture of 2,6-dimethylbicyclo[4.4.0]decan-1-ol constituted by preponderant and almost equivalent amounts of the isomers of formula (Ia) and (Ic), i.e. (1RS, 2SR, 6RS)-2,6-dimethylbicyclo[4.4.0]decan-1-ol and (1RS, 2RS, 6SR)-2,6-dimethylbicyclo[4.4.0]decan-1-ol, respectively. These two isomers were accompanied by minor amounts of isomer (Ib), viz. (1RS, 2SR, 6SR)-2,6-dimethylbicyclo[4.4.0]decan-1-ol.

For all practical purposes in accordance with the invention, the mixture obtained according to the method of Marshall can be used as such without prior separation of its isomers of prior enrichment of one of them. However, whenever desired, such a separation can be effected by column chromatography, for instance by making use of silica gel as support (eluent:hexane/ether). The thus obtained pure isomers showed the following analytical characteristics:

(1RS,2SR,6RS)-2,6-Dimethylbicyclo[4.4.0]decan-1-ol,
(Ia)

IR (neat): 3550, 1460, 1450, 1180, 1160, 1070, 1050, 1000, 965, 950, 900, 880, 830, 800 cm$^{-1}$;

NMR (90 MHz, CDCl$_3$); 0.86 (3H, d, 6); 0.97 (3H, s) δ ppm;

MS: 112 (100), 111 (25), 55 (20), 43 (19), 125 (14), 97 (11), 83 (10), 126 (9), 67 (9), 149 (3), 182 (1, M+), 164 (<1).

(1RS,2SR,6SR)-2,6-Dimethylbicyclo[4.4.0]decan-1-ol,
(Ib)

IR (neat): 3525, 1460, 1380, 950, 880 cm$^{-1}$;

NMR (90 MHz, CDCl$_3$): 1.02 (3H, d, 8); 1.10 (3H, s) δ ppm;

MS: 112 (100), 111 (25), 55 (18), 43 (18), 125 (16), 97 (9), 83 (8), 126 (7), 69 (7), 149 (7), 182 (<1, M+), 135 (<1), 164 (<1).

(1RS,2RS,6SR)-2,6-Dimethylbicyclo[4.4.0]decan-1-ol,
(Ic)

IR (neat): 3550, 1460, 1450, 1380, 1180, 1000, 950, 880 cm$^{-1}$;

NMR (90 MHz, CDCl$_3$): 0.78 (3H, d, 6.5); 1.04 (3H, s) δ ppm;

MS: 112 (100), 111 (24), 55 (20), 43 (19), 125 (14), 126 (11), 97 (10), 69 (9), 83 (8), 182 (3, M+), 149 (2), 135 (1), 167 (<1).

The invention is better illustrated by but not limited to the following example.

EXAMPLE

A base perfume composition of "Chypre" type for luxury perfumes was obtained by mixing the following ingredients (parts by weight):

| | |
|---|---|
| Synthetic bergamot oil | 200 |
| Coumarin | 100 |
| Cyclopentadecanolide | 100 |
| α-Isomethylionone | 100 |
| Absolute oak-moss 50%* | 120 |
| Acetylcedrene | 380 |
| Total | 1000 |

*in dipropylglycol

By adding to 100 g of the above base composition 0.2 g of a 1% by weight solution (in dipropyl glycol) of an isomeric mixture of 2,6-dimethyl[4.4.0]decan-1-ol (Ia:Ib:Ic in a weight ratio of 47:5:48 or 46:1:52) there was obtained a novel composition having a well distinct odorous character of ambery-woody type.

By replacing in the above example, the isomeric mixture by any of its constituents, there were obtained novel perfume compositions whose odorous character was sensibly similar to that observed by the use of the mixture itself; the effect was however more pronounced by using isomer (Ic).

What we claim is:

1. Process for imparting, enhancing or modifying the ambery odorous note in a perfume composition which comprises adding thereto a compound of formula

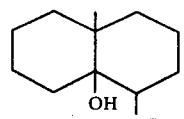

at a concentration of from about 1 to 100 parts per million by weight based on the total weight of the thus obtained material.

2. Process according to claim 1, wherein the compound of formula (I) is (1RS,2SR,6RS)-2,6-dimethyl-bicyclo[4.4.0]decan-1-ol.

3. Process according to claim 1, wherein the compound of formula (I) is (1RS,2RS,6SR)-2,6-dimethyl-bicyclo[4.4.0]decan-1-ol.

4. Process according to claim 1, wherein the compound of formula (I) is (1RS,2SR,6SR)-2,6-dimethyl-bicyclo[4.4.0]decan-1-ol.

5. A perfume composition containing as active perfuming ingredient an amount of a compound of formula (I) as set forth in claim 1 sufficient to impart an ambery odorous note thereto.

6. An artificial essential oil of Angelica roots which comprises having added thereto an amount of a compound of formula (I) as set forth in claim 1 sufficient to impart an ambery odorous note thereto.

* * * * *